US 7,238,832 B2

(12) United States Patent
Itahashi et al.

(10) Patent No.: US 7,238,832 B2
(45) Date of Patent: Jul. 3, 2007

(54) PRODUCTION METHOD OF A COUPLING COMPOUND

(75) Inventors: Tamon Itahashi, Ibaraki (JP); Takashi Kamikawa, Nara (JP)

(73) Assignee: Sumitomo Chemical Company, Limited, Osaka (JP)

( * ) Notice: Subject to any disclaimer, the term of this patent is extended or adjusted under 35 U.S.C. 154(b) by 499 days.

(21) Appl. No.: 10/781,198

(22) Filed: Feb. 18, 2004

(65) Prior Publication Data

US 2004/0167364 A1    Aug. 26, 2004

(30) Foreign Application Priority Data

Feb. 19, 2003    (JP)    ............... 2003-040759

(51) Int. Cl.
C07C 69/00    (2006.01)
C07C 45/00    (2006.01)
C07C 41/00    (2006.01)
C07C 22/00    (2006.01)
C07C 255/00   (2006.01)

(52) U.S. Cl. ............ 560/130; 568/312; 568/322; 568/323; 568/626; 570/144; 558/411

(58) Field of Classification Search ............ None
See application file for complete search history.

(56) References Cited

U.S. PATENT DOCUMENTS

| | | | | |
|---|---|---|---|---|
| 5,922,898 | A * | 7/1999 | Miller et al. ............. | 558/378 |
| 6,194,599 | B1 * | 2/2001 | Miller et al. ............. | 558/411 |
| 6,395,916 | B1 | 5/2002 | Buchwald et al. | |
| 7,041,856 | B2 * | 5/2006 | Itahashi et al. ............. | 568/642 |
| 2002/0016489 | A1 | 2/2002 | Marcuccio et al. | |
| 2003/0158419 | A1 | 8/2003 | Kamikawa et al. | |
| 2003/0162950 | A1 | 8/2003 | Itahashi et al. | |

FOREIGN PATENT DOCUMENTS

| | | |
|---|---|---|
| DE | 152 547 | 12/1981 |
| EP | 0 366 573 A1 | 5/1990 |
| WO | WO 00/68252 A1 | 11/2000 |

OTHER PUBLICATIONS

Akiharu Satake, "Synthesis of Neutral π-Allylpalladium Complexes having Bisnitrogen Ligands and Palladium-Catalyzed Cyclopropanation of Ketene Silyl Acetals with Allylic Acetates", Yukigosei Kagaku Kyokai-Shi, vol. 58, No. 8, pp. 736-744, (2000).
M.R. Netherton et al., "Suzuki Cross-Couplings of Alkyl Tosylates that Process β Hydrogen Atoms: Synthetic Studies", Angew. Chem. Int. Ed., vol. 41, No. 20, pp. 3910-3912, (2002).
Leadbeater et al., "Suzuki Aryl Couplings Mediated By Phosphine-Free Nickel Complexes", Tetrahedron, vol. 55, pp. 11889-11894, (1999).
Kirichhoff et al., "Boronic Acids: New Coupling Partners in Room-Temperature Suzuki Reactions of Alkyl Bromides. Crystallographic Characterization Of An Oxidative-Addition Adduct Generated under Remarkably Mild Conditions", Journal of American Chemical Society, vol. 124, No. 46, pp. 13662-13663, (2002).
Dunach et al., "Carbon-Carbon Bond Formation with Electrogenerated Nickel and Palladium Complexes", European Journal of Organic Chemistry, No. 9, pp. 1605-1622, (2003).

* cited by examiner

Primary Examiner—Sikarl A. Witherspoon
(74) Attorney, Agent, or Firm—Akin Gump Strauss Hauer & Feld LLP

(57) ABSTRACT

There is provided a method for producing a coupling compound of formula (1):

$$(Y-)_{(n-1)}R^1-R^2-(R^1)_{(n'-1)} \quad (1)$$

wherein $R^1$, $R^2$ n and n' are as defined below, Y is $R^2$ or X as defined below, which method comprises reacting an organic halogen compound of formula (2):

$$n'(R^1X^1_n) \quad (2)$$

wherein $X^1$ represents a bromine or iodine, $R^1$ represents a substituted or unsubstituted, linear, branched or cyclic hydrocarbon group of which α and β carbon atoms in relation to $X^1$ are sp3 carbon atoms, n and n' each independently represent an integer of 1 or 2, and provided that n and n' do not simultaneously represent 2, with an organic boron compound of formula (3):

$$m\{R^2(BX^2_2)_{n'}\} \quad (3)$$

wherein $R^2$ represents a substituted or unsubstituted aryl group or a substituted or unsubstituted alkenyl group and the boron atom is bonded with a sp2 carbon atom thereof, $X^2$ represents a hydroxyl or alkoxy group, n' is as defined above, m represents an integer of 1 or 2, and m is not more than n, in the presence of a catalyst comprising a) a nickel compound, and b) b-1) a compound of formula (i):

(i)

$_a(R^3)$ ... $(R^4)_b$ (with pyridine N atoms)

or b-2) a compound of formula (ii):

(ii)

$(R^6)_d$
$_c(R^5)$ ... $(R^7)_{e'}$ (phenanthroline-type with N atoms)

8 Claims, No Drawings

PRODUCTION METHOD OF A COUPLING COMPOUND

FIELD OF THE INVENTION

The invention relates to a cross-coupling catalyst and a method for producing the coupling compound, which are useful, for example, as liquid crystal materials, organic EL materials, pharmaceuticals, agricultural chemicals or synthetic intermediates thereof.

There are disclosed Suzuki cross-coupling reactions between aryl halide compounds and aryl boron compounds catalyzed by palladium phosphine complexes and also a coupling reaction between aryl halide compounds and aryl boron compounds catalyzed by nickel phosphine compounds or a nickel catalyst containing nickel compounds and triethylamine or dipyridyl (e.g. Tetrahedron 55(1999) 11889-11894).

It is also disclosed (for example, Angew. Chem. Int. Ed., pp. 3910-3912, 2002) that cross-coupling of alkyl halides, which are less reactive than aryl halides, requires an expensive palladium phosphine complex compound but the cross-coupling reaction using nickel compound is not known.

According to the present invention, a cross-coupling reaction between a halide compound of which carbon atoms at the α and β positions relative to the halogen atom are $sp^3$ carbon atoms and an organic boron compound of which boron atom is bonded with a $sp^2$ carbon atom thereof can be readily accomplished by using a catalyst containing inexpensive nickel compounds.

The present invention provides:

a method for producing a coupling compound of formula (1):

$$(Y—)_{(n-1)}R^1—R^2—(R^1)_{(n'-1)} \quad (1)$$

wherein $R^1$, $R^2$ n and n' are as defined below,

Y is $R^2$ or X as defined below, which method comprises reacting an organic halogen compound of formula (2):

$$n'(R^1X^1_n) \quad (2)$$

wherein $X^1$ represents a bromine or iodine, $R^1$ represents a substituted or unsubstituted, linear, branched or cyclic hydrocarbon group of which α and β carbon atoms in relation to $X^1$ are sp3 carbon atoms, n and n' each independently represent an integer of 1 or 2, and provided that n and n' do not simultaneously represent 2, with an organic boron compound of formula (3):

$$m\{R^2(BX^2_2)_{n'}\} \quad (3)$$

wherein $R^2$ represents a substituted or unsubstituted aryl group or a substituted or unsubstituted alkenyl group and the boron atom is bonded with a sp2 carbon atom thereof, $X^2$ represents a hydroxyl or alkoxy group, n' is as defined above, m represents an integer of 1 or 2, and m is not more than n, in the presence of a catalyst comprising a) a nickel compound, and b) b-1) a compound of formula (i):

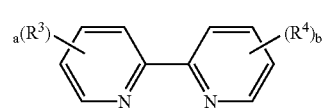

wherein $R^3$ and $R^4$ each independently represent an alkyl, aryl, alkenyl, alkynyl, alkoxyl, hydroxy, sulfo, alkyloxycarbonyl, aryloxycarbonyl, carbamoyl, cyano, isocyano, cyanato, isocyanato or formyl group, or a hydrocarbylsilyl group, and optionally two adjacent groups among $R^3$ and $R^4$ groups with the carbon atoms to which they are bonded form a ring such as 5- or 6-membered ring (e.g, benzene ring), a and b are the same or different and independently represent an integer of 0 to 4, or b-2) a compound of formula (ii):

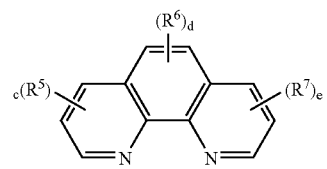

wherein $R^5$, $R^6$ and $R^7$ groups are the same or different and independently represent a hydrogen atom, an alkyl, aryl, alkenyl, alkynyl, alkoxyl, hydroxy, hydroxyalkyl, sulfo, alkyloxycarbonyl, aryloxycarbonyl, carbamoyl, cyano, isocyano, cyanato, isocyanato or formyl group, or a hydrocarbylsilyl group, and optionally two adjacent groups among $R^5$, $R^6$, and $R^7$ groups with the carbon atoms to which they are bonded form a ring such as 5- or 6-membered ring (e.g, benzene ring), c, and e are the same or different and independently represent an integer of 0 to 3, and d represents an integer of 0 to 2; or a mixture thereof.

DETAILED DESCRIPTION OF THE INVENTION

A description is made to the embodiments of the present invention in detail below.

Examples of the nickel compound used in the present invention include, for example, compounds of divalent or zero-valent nickel, and specifically a nickel salt, a complex salt of a divalent nickel compound, nickel hydroxide, a π complex compound of divalent or zero-valent nickel.

For example, the nickel salt is a salt of nickel and an inorganic or organic acid. Examples of the nickel salt of the inorganic acid include, for example, a nickel halide such as nickel(II) chloride, nickel(II) bromide and nickel(II) iodide, nickel(II) nitrate, nickel(II) sulfate, nickel(II) ammonium sulfate, and nickel(II) hypophosphite.

Examples of the nickel salt of the organic acid include, for example, nickel(II) acetate, nickel(II) formate, nickel(II) stearate, nickel(II) cyclohexanebutyrate, nickel(II) citrate, and nickel(II) naphthenate.

Examples of the complex salt of the divalent nickel compound include, for example, an amine complex of divalent nickel such as nickel(II) hexaamine chloride or nickel(II) hexaamine iodide, and an acetylacetone complex salt of divalent nickel such as nickel acetylacetonate.

Examples of the nickel hydroxide include, for example, nickel(II) hydroxide.

Examples of the π complex compound of divalent nickel include, for example, bis(η³-allyl)nickel(II), bis(η-cyclopentadienyl)nickel(II) and allylnickel chloride dimer.

Examples of the π complex compound of zero-valent nickel include, for example, bis(1,5-cyclooctadiene)nickel (0) and nickelcarbonyl(0).

Such nickel compounds may be an anhydride or a hydrate.

Preferred nickel compound are nickel chloride, nickel bromide, nickel iodide, nickel nitrate, nickel acetate, and bis(1,5-cyclooctadiene)nickel(0).

The nickel compound may be used in an amount of 0.00001 mole to 1 mole, preferably in a catalytically effective amount such as 0.00001 mole to 0.2 mole, per mol of the halogen atom of the organic halide to be reacted.

The compound of formula (i) or (ii) may be supported on a carrier such as a reaction solvent-insoluble resin so that the reaction can be carried out in a heterogeneous system.

The compound of formula (i) or (ii) is used, for example, in an amount of about at least 0.1 mol, and preferably 1 to 10 moles, per mol of the nickel atom of the nickel compound. In the process of the present invention, the compound of formula (i) or (ii) may be used in combination with any phosphine compound.

The catalyst may be prepared by contacting the nickel compound and the compound of formula (i) or (ii) and isolating the resulting compound comprising the nickel compound and the compound of formula (i) or (ii), which is typically coordinated thereto.

Alternatively, a catalyst preparation in a solution form, prepared by contacting the components a) and b) in a suitable solvent, may be used in the coupling reaction as it is.

Alternatively, the nickel compound and the compound of formula (i) or (ii) may be independently added, as catalyst components, to the reactants of formula (2) and (3), typically in a suitable solvent.

A reducing agent may be reacted with the divalent nickel compound, as the catalyst component, or the catalyst comprising the nickel compound. Any reducing agent may be used without limitation, and preferred examples thereof include, for example, sodium borohydride, lithium aluminum hydride, sodium hydride, diisobutyl aluminum hydride, an alkyl Grignard reagent, alkyl lithium, and zinc metal. For example, the catalyst may be typically prepared by adding the divalent nickel compound, the compound of formula (i) or (ii) and the reducing agent, and optionally a suitable solvent, which is inert to the reducing agent, in an optional order. Examples of the solvent include, for example, those solvents that may be used in the coupling reaction as shown below, and an ether solvent or a hydrocarbon solvent is preferably used.

The nickel compound may be used, for example, in a completely dissolved form or suspended form in the reaction system containing the reactants and optionally a suitable solvent employed. The nickel compound may be used as it is or may be supported on a material such as carbon, silica or alumina that are insoluble to the reaction solvent and reactants.

The compound of formula (i) and (ii) according to the invention is described in detail below.

$R^3$ and $R^4$ will be explained below.

Examples of the alkyl group include, for example, a C1-10 alkyl group such as a methyl, ethyl, propyl, i-propyl, pentyl, heptyl, octyl, nonyl, decyl, cyclopentyl, or cyclohexyl group.

Examples of the aryl group include, for example, a phenyl, or naphthyl group.

Examples of the alkenyl group include, for example, a C2-8 linear, branched or cyclic alkenyl such as vinyl, propenyl, butenyl, pentenyl, hexenyl, cyclopentenyl, cyclohexenyl, or cyclooctadienyl group.

Examples of the alkynyl group include, for example, a propynyl group.

Examples of the alkoxyl group include, for example, a C1-10 alkoxy group such as a methoxy, ethoxy, hexyloxy, cyclohexyloxy, heptyloxy, octyloxy, nonyloxy, or decyloxy group.

Examples of the alkyloxycarbonyl group include, for example, an alkoxy(C1-10)carbonyl group such as a methyloxycarbonyl, ethoxycarbonyl, propoxycarbonyl, butoxycarbonyl, pentyloxycarbonyl, hexyloxycarbonyl, heptyloxycarbonyl, octyloxycarbonyl, nonyloxycarbonyl, or decyloxycarbonyl group.

Examples of the aryloxycarbonyl group include, for example, a phenyloxycarbonyl or naphtyloxycarbonyl group.

Examples of the hydrocarbysilyl group include, for example, trimethylsilyl, tripheylsilyl, or t-butyldimethylsilyl group.

When two adjacent groups among $R^3$ and $R^4$ groups with the carbon atoms to which they are bonded form a benzene ring, the bipyridyl moiety represents 2,2'-biquinolinyl.

Preferably, a and b are an integer of 0 to 3. Preferred $R^3$ and $R^4$ groups are alkyl when a and b are not 0. More preferably, a and b are both 0, which corresponds to dipyridyl.

Specific examples of the compound of formula (i) include, for example, dipyridyl, 4,4'-dimethyl-2,2'-dipyridyl, 4,4'-diphenyl-, 2,2'-dipyridyl, 5,5-dimethyl-2,2'-dipyridyl, 4,4'-di-t-butyl-2,2'-dipyridyl, 6-methyl-2,2'-dipyridyl, 2,2'-biquinoline, 6,6'-bi-2-picoline, 2,2'-bi-4-lepidine, 4,4'-dinonyl-2,2'-dipyridyl, 2,2'-dipyridyl-3,3'-diol, 2,2'-biquinolinyl-4,4'-dicarboxylic acid dibutyl ester, and 4,4'dimethoxy-2,2'-dipyridyl.

Examples of the groups represented by $R^5$ to $R^7$ include, those described above for $R^3$ and $R^4$.

Preferably, c and e are 0 to 2. Preferred $R^5$ to $R^7$ are alkyl when c and e are 1 or 2. More preferably, c, d and e are 0, which corresponds to 1,10-phenanthroline.

Specific examples of the compound of formula (ii) include, for example, 2,9-dimethyl-4,7-diphenyl-1,10-phenanthroline, 2,9-dimethyl-1,10-phenanthroline, 3,4,7,8-tetramethyl-1,10-phenanthroline, 4,7-dihydroxy-1,10-phenanthroline, 4,7-diphenyl-1,10-phenanthroline, 4-methyl-1,10-phenanthroline, 5-methy-1,10-phenanthroline, 5-phenyl-1,10-phenanthroline, 4,7-dimethyl-1,10-phenanthroline, 5,6-dimethyl-1,10-phenanthroline, 1,10-phenanthroline-2,9-dimethanol, and 2,9-di-n-butyl-1,10-phenanthroline.

As for the compounds of formula (i) and (ii), JP2000-311723A may be referred to, or the compounds such as those specified above are commercially available, for example, from Aldrich Company, Ltd., Wako Pure Chemical Industries, Ltd, or Nacalai Tesque, Inc.

Examples of the present coupling reaction include, for example, when n=n'=1,

(1a);

when n=2 and n'=1 (m=1),

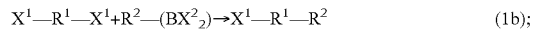

(1b);

when n=2 and n'=1 (m=2),

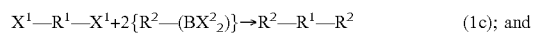

(1c); and when n=1 and n'=2,

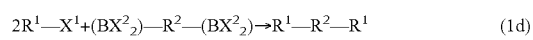

(1d)

The amounts of the organic halogen compound (2) and the organic boron compound (3) are typically set in a range that covers stoichiometric amount, which may be calculated based on the reaction schemes above but are not limited thereto, and are suitably set by taking account of the desired compound, selectivity and separation procedure of the resulting products as described below, alternatively the amounts may be set in such amounts that are suitable to conduct the reactions such as (1c) or (1d) in a step-by-step fashion, if necessary.

The organic halide in the embodiments of the present coupling reaction is described in detail below.

In the coupling reaction, $X^1$ is eliminated in the reaction with the boron compound, whereby a new carbon-carbon bond is formed between the carbon atoms, which were bonded with the boron atom and the halogen atom respectively. The $sp^3$ carbon atom at α position relative to $X^1$ means an $sp^3$ carbon atom bonded with the halogen atom, and the $sp^3$ carbon atom at β position relative to $X^1$ is an $sp^3$ carbon atom bonded with the $sp^3$ α carbon atom. More preferably, the carbon atoms at α, β and γ positions relative to the halogen atom are $sp^3$ carbon atoms.

Examples of the substituted or unsubstituted, linear, branched or cyclic hydrocarbon group in which α and β carbon atoms relative to $X^1$ are $sp^3$ carbon atoms, represented by $R^1$, include, for example, a linear, branched or cyclic $C_{2-30}$ alkyl group, and specific examples thereof include, for example, ethyl, propyl, isopropyl, butyl, pentyl, hexyl, heptyl, octyl, nonyl, decyl, undecyl, dodecyl, tridecyl, tetradecyl, octadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl, cyclopentyl, cyclohexyl, and adamantyl.

Examples of the substituted or unsubstituted, linear, branched or cyclic hydrocarbon group of which α and β carbon atoms relative to $X^1$ are $sp^3$ carbon atoms, represented by $R^1$, include, for example, a linear, branched or cyclic $C_{4-30}$ alkenyl group, and specific examples thereof include, for example, butenyl, pentenyl, hexenyl, heptenyl, octenyl, nonenyl, decenyl, undecenyl, dodecenyl, tridecenyl, tetradecenyl, octadecenyl, hexadecenyl, heptadecenyl, octadecenyl, nonadecenyl, icosenyl, henicosenyl, docosenyl, tricosenyl, tetracosenyl, pentacosenyl, hexacosenyl, heptacosenyl, octacosenyl, nonacosenyl, triacontenyl, cyclopentenyl, and cyclohexenenyl.

Examples of the substituent of the substituted linear, branched or cyclic hydrocarbon group of which α and β carbon atoms relative to $X^1$ are $sp^3$ carbon atoms include, for example, a fluorine atom, a hydroxyl group,
- an alkoxyl group such as methoxy, ethoxy or tert-butoxy,
- an aryloxy group such as phenoxy group,
- a mercapto group,
- an alkylthio group such as methylthio,
- an arylthio group such as phenylthio,
- a cyano group, a nitro group, an amino group,
- an mono- or di-alkylamino group such as dimethylamino or cyclohexylamino,
- an alyl- or aryl-carbamate group such as tert-butylcarbamate, methylcarbamate, or phenylcarbamate,
- an aryl- or alkyl-sulfonamide group such as benzenesulfonamide or methanesulfonamide,
- an aryl- or alkyl-imino or imide group such as phthalimide,
- a formyl group, a carboxyl group,
- an alkoxycarbonyl group such as methoxycarbonyl,
- an aryloxycarbonyl group such as p-methoxyphenoxycarbonyl or phenoxycarbonyl,
- a carbamoyl,
- an N-alkyl- or N-aryl-carbamoyl such as N-phenylcarbamoyl,
- a heterocylic group such as pyridyl, quinazolinyl, pyrimidyl, furyl, thienyl, pyrrolyl, and imidazolyl, and
- an aryl group such as phenyl, or naphthyl. The term "alkyl" contained in the substituents in the preceding paragraph typically means $C_{1-8}$ alkyl group such as methyl, ethyl, propyl, butyl, pentyl, hexyl, heptyl, or octyl, and the term "aryl" contained in the substituents in the preceding paragraph typically means $C_{6-10}$ aryl group such as phenyl, naphthyl, tolyl, xylyl or anisyl.

Two substituents on adjacent carbon atoms of $R^1$ may be bonded to form a condensed ring together with $R^1$. Any of these substituents may also be substituted.

Examples of the organic halide include, for example, 1-bromopropane, 1-bromobutane, 1-bromopentane, 1-bromohexane, 1-bromoheptane, 1-bromooctane, 1-bromononane, 1-bromodecane, 1-bromododecane, 1-bromotridecane, 1-bromotetradecane, 1-bromopentadecane, 1-bromohexadecane, 1-bromooctadecane, 1-bromoeicosane, 1-bromodocosane, 2-bromopropane, 1-bromo-2-methylpropane, 2-bromopentane, 3-bromopentane, (S)-(+)-1-bromo-2-methylbutane, 1-bromo-3-methylbutane, 1-bromo-2,2-dimethylpropane, 1-bromo-2-ethylethane, 2-bromoheptane, 2-ethylhexyl bromide, 2-bromodecane, 2-bromododecane, 2-bromotridecane, 1,2-dibromoethane, 1,3-dibromopropane, 1,4-dibromobutane, 1,5-dibromopentane, 1,6-dibromohexane, 1,7-dibromoheptane, 1,8-dibromooctane, 1,9-dibromononane, 1,10-dibromodecane, 1,11-dibromoundecane, 1,12-dibromododecane, 2-bromo-1-chloropropane, 1,2-dibromopropane, 1,2-dibromobutane, 1,3-dibromobutane, 2,3-dibromobutane, 1-bromo-3-chloro-2-methylpropane, 1,2-dibromo-2-methylpropane, 1,4-dibromopentane, 1,2-dibromo-3,3-dimethylbutane, 1-bromoheptadecafluorooctane, 4-bromo-1-butene, 5-bromo-1-pentene, 6-bromo-1-hexene, 5-bromo-2-methyl-2-pentene, 8-bromo-1-octene, (R)-(−)-citronellyl bromide, (R)-(+)-citronellyl bromide, cyclobutyl bromide, cyclohexyl bromide, cycloheptyl bromide, (bromomethyl)cyclohexane, 3-bromopropanol, (R)-3-bromo-2-methyl-1-propanol, 8-bromo-1-octanol, 9-bromo-1-nonanol, 10-bromo-1-decanol, 11-bromo-1-undecanol, 12-bromo-1-dodecanol, 1,4-dibromo-2-butanol, 1,3-dibromo-2-propanol, 2-bromoethyl methyl ether, 2-bromoethyl ethyl ether, 2-bromoethyl ether, bromomethyl octyl ether, 1-iodopropane, 1-iodobutane, 1-iodopentane, 1-iodohexane, 1-iodoheptane, 1-iodooctane, 1-iodononane, 1-iododecane, 1-iodododecane, 1-iodotridecane, 1-iodotetradecaen, 1-iodopentadecane, 1-iodohexadecane, 2-iodopropane, 2-iodobutane, 1-iodo-2-methylpropane, (S)-(+)-1-iodo-2-methylbutane, 1-iodo-2,2-dimethylpropane, 1,2-diiodoethane, 1,3-diiodopropane, 1,4-diiodobutane, 1,5-diiodopentane, 1,6-diiodohexane, 1,8-diiodooctane, 1,10-diiododecane, perfluorobutyl iodide, 1-iodoheptadecafluorooctane, 1,1,1,2,2,3,3,4,4,5,5,6,6-tridecafluoro-8-iodooctane, 1,1,1,2,2,3,3,4,4,5,5,6,6,7,7,8,8-heptadecafluoro-10-iodo-decane, perfluorodecyl iodide, perfluorododecyl iodide, and cyclohexyl iodide.

In the organic boron compound of formula (3), examples of the substituted or unsubstituted aryl group represented by $R^2$ include, for example, any aryl group including those having one to four aryl rings, and preferably having 6 to 16 carbon atoms.

Examples of the unsubstituted aryl group include, for example, phenyl, naphthyl, anthracenyl, phenanthryl, indenyl, fluorenyl, and pyrenyl.

Examples of the unsubstituted heteroaryl group represented by $R^2$ include, for example, pyridyl, quinazolyl, quinolyl, pyrimidyl, furyl, thienyl, pyrrolyl, imidazolyl, and tetrazolyl.

In the organic boron compound of formula (3), when $R^2$ is an alkenyl group, the boron atom is bonded with a $sp^2$ carbon atom of the alkenyl carbon-carbon double bond, which may also be conventionally referred to as a "vinyl carbon atom".

Examples of the alkenyl group represented by $R^2$ include, for example, vinyl, 1-propenyl and those shown as the examples of the alkenyl group represented by $R^1$ of the organic halide of formula (1).

Preferred alkenyl group are a substituted or unsubstituted $C_2$ to $C_{10}$ alkenyl group having one or more double bonds.

Examples of the substituted aryl, heteroaryl and alkenyl groups include, for example, the aryl, heteroaryl and alkenyl groups substituted with at least one group selected from those substituent groups as exemplified for the substituent group of the substituted linear, branched or cyclic hydrocarbon group represented by $R^1$.

Examples of the substituted aryl include, for example, an aryl substituted with an alkylenedioxy group such as methylenedioxy or a dialkylaminoalkyl group such as dimethylaminomethyl.

Examples of the alkoxy group represented by $X^2$ include, for example, methoxy, ethoxy propoxy, butoxy, pentyloxy, hexyloxy, heptyloxy, or octyloxy. Alternatively two alkoxyl groups are bonded to form, for example, an alkylendioxy (e.g. dimethylenedioxy, trimethylenedioxy or pinacoloxy ) or arylenedioxy group (e.g. catecholoxy). Specific examples of the boron compound include, for example, boronic acid-pinacol ester or boronic acid-catechol ester. When $R^2$ groups form a residue of a boronic acid trimer anhydride, $X^2_2$ represent —O—B($R^2$)—O—B($R^2$)—O—.

When $R^2$ group represents the substituted aryl or heteroaryl group or represents an ortho-condensed, or ortho and peri-condensed polycyclic aromatic ring, one of the ortho positions of the $BX^2_2$ group preferably is unsubstituted.

A preferred boron compound of formula (2) wherein $R^2$ is an aryl group is a compound of formula (4):

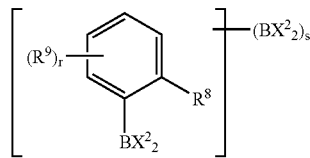

(4)

wherein $R^8$ represents a hydrogen atom, $X^2$ groups independently represent a hydroxy group or an alkoxy group, or the alkoxy groups together form an alkylenedioxy group (e.g. dimethylene, trimethylene or pinacol alcohol residue), or $X^2_2$ represent —O—B($R^{20}$)—O—B($R^{21}$)—O—, wherein $R^{20}$ represents the phenyl residue as defined in connection with formula (4) above, r represents an integer of 0 to 4, s represents 0 or 1, and r+s≦4 when the benzene ring does not form a condensed polycyclic aromatic ring, $R^9$ groups are the same or different and independently represent a substituted or unsubstituted aryl group, a substituted or unsubstituted heteroaryl group, or a substituted or unsubstituted linear, branched or cyclic alkenyl group, or $R^9$ groups on adjacent carbon atoms of the benzene ring are optionally bonded to form a condensed polycyclic aromatic ring, for example, in which the $R^9$ groups are ortho-condensed (e.g. naphthalene, anthracene, phenanthrene), or ortho and peri-condensed with the benzene ring (e.g. pyrene). Preferably, the ortho position of the $BX^2_2$ group is unsubstituted, that is, a hydrogen atom. As for the examples of the substituted or unsubstituted aryl, heteroaryl, or alkenyl group represented by $R^9$, those examples and descriptions of the aryl, heteroaryl, or alkenyl group for $R^2$ are referred to.

When $X^2$ is a hydroxy group, the boron compound of formula (3) may form an acid anhydride of formula (5) below.

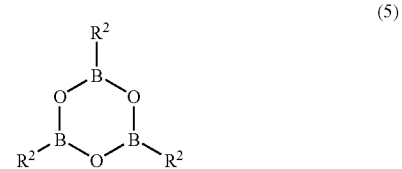

(5)

wherein $R^2$ is as defined in connection with formula (3).

Examples of the boron compound (3) include, for example, phenylboronic acid, 2-methylphenylboronic acid, 3-methylphenylboronic acid, 4-methylphenylboronic acid, 2,3-dimethylphenylboronic acid, 4-dimethylphenylboronic acid, 2,5-dimethylphenylboronic acid, 2-ethylphenylboronic acid, 4-n-propylphenylboronic acid, 4-isopropylphenylboronic acid, 4-n-butylphenylboronic acid, 4-tert-butylphenylboronic acid, 1-naphthylboronic acid, 2-naphthylboronic acid, 2-biphenylboronic acid, 3-biphenylboronic acid, 4-biphenylboronic acid, 2-fluoro-4-biphenylboronic acid, 2-fluorenylboronic acid, 9-fluorenylboronic acid, 9-phenanthrenylboronic acid, 9-anthracenylboronic acid, 1-pyrenylboronic acid, 2-trifluoromethylphenylboronic acid, 3-trifluoromethylphenylboronic acid, 4-trifluorophenylboronic acid, 3,5-bis(trifluoromethyl)phenylboronic acid, 2-methoxyphenylboronic acid, 3-methoxyphenylboronic acid, 4-methoxyphenylboronic acid, 2,5-dimethoxyphenylboronic acid, 4,5-dimethoxyphenylboronic acid, 2,4-dimethoxyphenylboronic acid, 2-ethoxyphenylboronic acid, 3-ethoxyphenylboronic acid, 4-ethoxyphenylboronic acid, 4-phenoxyboronic acid, 3,4-methylenedioxyphenylboronic acid, 2-fluorophenylboronic acid, 3-fluorophenylboronic acid, 4-fluorophenylboronic acid, 2,4-difluorophenylboronic acid, 2,5-difluorophenylboronic acid, 4,5-difluorophenylboronic acid, 3,5-difluorophenylboronic acid, 2-formylphenylboronic acid, 3-formylphenylboronic acid, 4-formylphenylboronic acid, 3-formyl-4-methoxyphenylboronic acid, 2-cyanophenylboronic acid, 3-cyanophenylboronic acid, 4-cyanophenylboronic acid, 3-nitrophenylboronic acid, 3-acetylphenylboronic acid, 4-acetylphenylboronic acid, 3-trifluoroacetylphenylboronic acid, 4-trifluoroacetylphenylboronic acid, 4-methylthiophenylboronic acid, 4-vinylphenylboronic acid, 3-carboxyphenylboronic acid, 4-carboxyphenylboronic acid, 3-aminophenylboronic acid, 2-(N,N-dimethylamino)phenylboronic acid, 3-(N,N-dimethylamino)phenylboronic acid, 4-(N,N-dimethylamino)phenylboronic acid, 2-(N,N-diethylamino)phenylboronic acid, 3-(N,N-diethylamino)phenylboronic acid, 4-(N,N-diethylamino)phenylboronic acid, 2-(N,N-dimethylaminomethyl)phenylboronic acid, furan-2-boronic acid, furan-3-boronic acid, 4-formyl-2-furanboronic acid, dibenzofuran-4-boronic acid, benzofuran-2-boronic acid, thiophene-2-boronic acid, thiophene-3-boronic acid, 5-methylthiophene-2-boronic acid, 5-chlorothiophene-2-boronic acid, 4-methylthiophene-2-boronic acid, 5-methylthiophene-2-boronic acid, 2-acetylthiophene-5-boronic acid, 5-methylthiophene-2-boronic acid, benzothiophene-2-boronic acid, dibenzothiophene-4-boronic acid, pyridine-3-boronic acid, pyridine-4-boronic acid, pyrimidine-5-boronic acid, quinoline-8-boronic acid, isoquinoline-4-boronic acid, 4-benzenebis (boronic acid), phenylboronic acid-pinacol ester, and 4-cyanophenylboronic acid-pinacol ester.

Examples of the base that may be used include, for example, an inorganic base such as a hydroxide, carbonate, hydrogencarbonate, phosphate, carboxylate or alkoxide of an alkali metal (e.g., sodium, potassium, lithium) or alkaline earth metal (e.g. barium, calcium). The base may be an anhydrous or hydrate form. The base is preferably a hydroxide, carbonate, hydrogencarbonate, phosphate, or carboxylate of the alkali metal or the alkaline earth metal, and more preferably a carbonate or phosphate of the alkali metal or the alkaline earth metal.

Preferred examples of the alkali metal or alkaline earth metal salt include, for example, lithium carbonate, sodium carbonate, potassium carbonate, cesium carbonate, calcium carbonate, barium carbonate, lithium phosphate, sodium phosphate, and potassium phosphate. Sodium carbonate, potassium carbonate or potassium phosphate is more preferred.

The base is usually used in an amount of about 0.1 to 20 moles, preferably 1 to 5 moles, per mol of the boron atom of the boron compound (3). Two or more bases may be used in combination.

The embodiments of the process of the present invention is generally performed using a solvent such as an organic solvent or water or mixtures thereof, preferably in the organic solvent.

Examples of the organic solvent include, for example, an alcohol solvent such as methanol or ethanol; an aprotic polar organic solvent such as N-methylpyrolidone, N,N-dimethylformamide, N,N-dimethylacetamide, dimethylsulfoxide, and acetonitrile; an ether solvent such as diethyl ether, diisopropyl ether, ethylene glycol dimethyl ether, diethylene glycol dimethyl ether, 1,4-dioxane, and tetrahydrofuran; an aromatic hydrocarbon solvent such as benzene, toluene and xylene; and an aliphatic hydrocarbon solvent such as hexane and heptane. One of these solvents may be used alone, or two or more of these solvents may be used in combination. The solvent is used in an amount of generally 1 to 200 times, preferably 5 to 100 times as much as the weight of the organic halide. In particular, the ether or aprotic polar organic solvent is preferred.

The reaction temperature is generally from 0° C. to 200° C., preferably from 20° C. to 140° C., depending on the structure of the organic halide.

The reaction is preferably performed under an inert gas atmosphere so that deactivation of the catalyst due to oxygen can be prevented. For example, the inert gas may be nitrogen or argon. The reaction may be performed under any pressure (e.g. from pressurized pressure to reduced pressure), but generally under atmospheric pressure.

In the embodiments of the process of the present invention, the organic halide (2), the boron compound (3), the compound of formula (i) or (ii), and the nickel compound, the base, and optionally an appropriate solvent are used and may be added in any order. In the process using a reducing agent that can react with the organic halide or the boron compound, the compounds to be used should be added in such order that the reducing agent can be prevented from reacting with the halide or the boron compound. For example, such a process maybe conducted by adding the organic halide, the boron compound and the base, and optionally an appropriate solvent in any order and then adding, to such a system, a mixture prepared from the nickel compound, the compound of formula (i) or (ii) and the reducing agent. Alternatively, such a process may be conducted, for example, by preparing a mixture of the nickel compound, the compound of formula (i) or (ii) and the reducing agent, and then adding to the resulting mixture the organic halide, the boron compound and the base, and optionally an appropriate solvent in optional order. In such a process, a compound comprising the nickel compound and the compound of formula (i) or (ii) coordinated thereto may be used in place of the mixture of the nickel compound and the compound of formula (i) or (ii).

After the reaction, the resulting coupling compound can be separated from the reaction mixture typically by adding an aqueous solution of mineral acid such as dilute hydrochloric acid or dilute sulfuric acid to the reaction liquid to acidify it, then typically performing extraction with an organic solvent, washing with water, and removing the solvent by distillation. If desired, the resulting coupling compound may further be purified by any method such as distillation, recrystallization and/or chromatography.

Examples of the coupling compound (1) include, for example, 1-isopropyl-4-n-nonylbenzene, 2-(2,5-difluorophenyl)butane, 1,6-diphenylhexane, 1-(N,N-dimethylaminophenyl)heptadecafluorooctane, 1-cyclohexyl-2-trifluorophenylbenzene, 12-(4-cyanophenyl)-1-dodecanol, 2-(4-methylenedioxyphenyl)ethyl methyl ether, 6-(9-anthracenyl)-1-hexene, 1-(3-acetylphenyl)-2-methylpropane, 1-(2-ethoxyphenyl)pentane, and 1-(3,4-methylenedioxyphenyl)butane.

EXAMPLE

The present invention is explained by way of examples in detail, however, the present invention is not limited thereto.

Yields of the compounds in the following Tables are determined by gas-chromatography analysis (GC-IS method) of reaction mixtures, or isolation operation in terms of organic halogen compound.

Example 1

Under argon atmosphere, 0.4 mmol (48 mg) of phenylboronic acid, 0.3 mmol (57 mg) of 1-bromooctane, 0.45 mmol (95 mg) of potassium phosphate and 0.015 mmol (3.0 mg) of 1,10-phenanthroline and 0.015 mmol (4.1 mg) of bis(1,5-cyclooctadiene)nickel were mixed in 1 ml of N,N-dimethylacetamide. Then, the reaction mixture was heated to 80° C., and stirred for 2 hours at the temperature. After completion of the reaction, the reaction mixture was cooled to room temperature. Then, 10 ml of 1N aqueous hydrochloric acid were added to dissolve excess of potassium phosphate, and the reaction solution was transferred to separatory funnel, and extracted with ethyl acetate. The organic phase was washed with saturated sodium chloride solution.

Yield by GCIS method of octylbenzene was 79% in terms of 1-bromooctane. The results are shown in Table 1.

Examples 2 to 4

In Example 2 to 4, the experiments were carried out in a similar manner as in Example 1 except that 0.4 mmol of the boron compounds as shown in Table 1 were used in place of p-methoxyphenylboronic acid, 0.015 mmol of the compounds shown in Table were used instead of 1,10-phenanthroline, 0.30 mmol of the organic halide compound shown in Table 1 was used instead of 1-bromooctane, and the solvent listed in Table 1 was used instead of N,N-dimethylacetamide.

The yields of Examples 2 and 3 in Table 1 were determined by GC-IS method and the yield in Example 4 was an isolated yield.

In Tables 1 and 2, solvents are abbreviated as follows: DMA: N,N-dimentylacetamide, DMF: N,N-dimethylformamide, NMP: N-methylpyrolidone, THF: Tetrahydrofuran Digyme: Diethyleneglycol dimethyl ether.

TABLE 1

| Example | Organic Halogen Compound | Organic Boron Compound | Compound | Solvent | Yield (%) |
|---|---|---|---|---|---|
| 1 | CH₃(CH₂)₇Br (1-bromooctane) | (HO)₂B–C₆H₅ (phenylboronic acid) | 1,10-phenanthroline | DMA | 79 |
| 2 | ↑ | ↑ | ↑ | NMP | 79 |
| 3 | ↑ | ↑ | 2,2'-bipyridine | DMF | 74 |
| 4 | ↑ | (HO)₂B–(o-tolyl) (2-methylphenylboronic acid) | 1,10-phenanthroline | ↑ | 51 |

Examples 5 to 34

In Examples 5-34, the experiments are conducted in a similar manner as in Example 1 except that 0.4 mmol of boronic acid compounds shown in Table 2 are used in place of p-methoxyphenylboronic acid, and 0.015 mmol of the compounds shown in Table 2 are used instead of 1,10-phenanthroline, 0.30 mmol of the halogenated organic compounds shown in Table 2 are used instead of 1-bromooctane, and the solvents shown in Table 2 are used instead of N,N-dimethylacetamide. Desired compounds as shown in Table 2 are obtained.

TABLE 2

| Ex. | Organic Halogen Compound | Organic Boron Compound | Compound |
|---|---|---|---|
| 5 | CH₃O–CH₂CH₂CH₂–I (1-iodo-3-methoxypropane) | (HO)₂B–C₆H₄–OCH₃ (4-methoxyphenylboronic acid) | 1,10-phenanthroline |
| 6 | CH₃(CH₂)₅CH₂–I (1-iodohexane) | (HO)₂B–C₆H₄–CF₃ (4-(trifluoromethyl)phenylboronic acid) | ↑ |
| 7 | ↑ | ↑ | 4,5-dimethyl-1,10-phenanthroline |
| 8 | ↑ | ↑ | 5,5'-dimethyl-2,2'-bipyridine |
| 9 | ↑ | (HO)₂B–C₆H₃(CH₃)₂ (3,4-dimethylphenylboronic acid) | 2,2'-bipyridine |
| 10 | ↑ | phenylboronic acid 1,3-propanediol ester | ↑ |

TABLE 2-continued

| # | Col A | Col B | Col C |
|---|---|---|---|
| 11 | ↑ | 3-acetoxyphenylboronic acid | 1,10-phenanthroline |
| 12 | 7-bromoheptyl acetate | 3-methoxy-5-methylphenylboronic acid | ↑ |
| 13 | ↑ | phenylboronic acid | ↑ |
| 14 | ↑ | ↑ | ↑ |
| 15 | ↑ | 2-naphthylboronic acid | 4,4'-di-tert-butyl-2,2'-bipyridine |
| 16 | ↑ | ↑ | 5-methyl-1,10-phenanthroline |
| 17 | ↑ | ↑ | 4-methyl-2,2'-bipyridine |
| 18 | ↑ | ↑ | 3,4,7,8-tetramethyl-1,10-phenanthroline |
| 19 | ↑ | ↑ | 2,2'-biquinoline |
| 20 | 1-bromo-7-octanone derivative | 3,5-difluorophenylboronic acid | ↑ |
| 21 | ↑ | ↑ | ↑ |

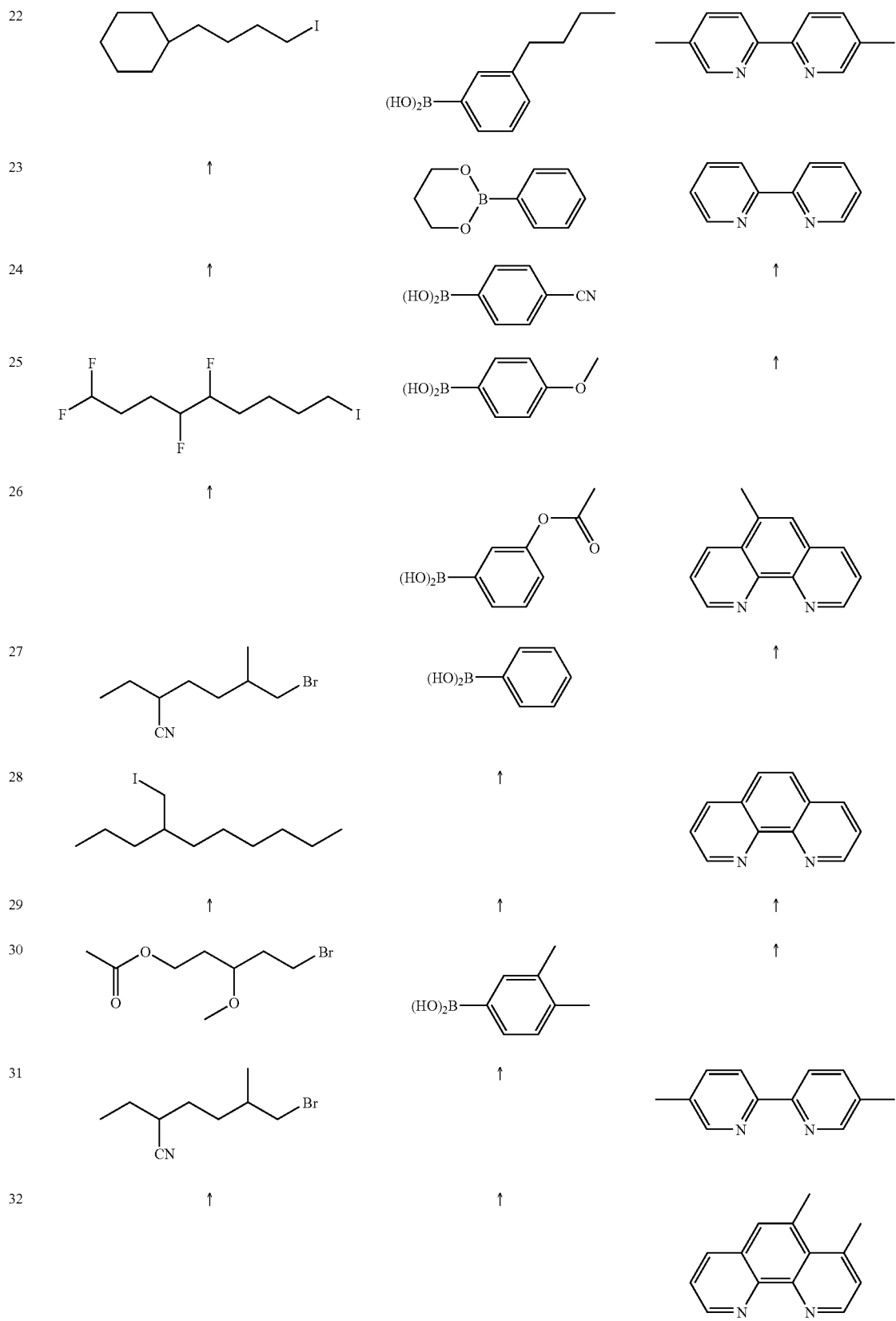

TABLE 2-continued
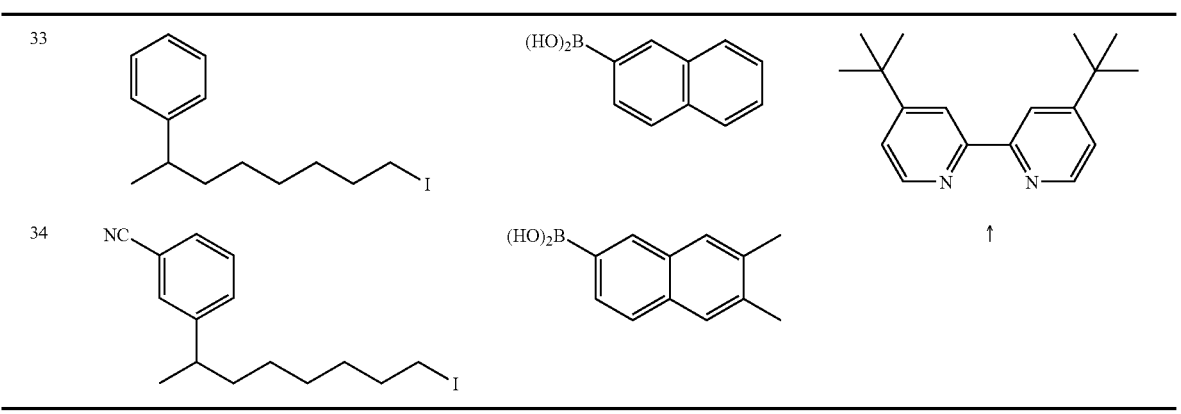
| Ex. | Solvent | Coupling Compound |
|---|---|---|
| 5 | DMA | |
| 6 | ↑ | |
| 7 | ↑ | ↑ |
| 8 | DMF | ↑ |
| 9 | ↑ | |
| 10 | ↑ | |
| 11 | NMP | |
| 12 | DMF | |
| 13 | ↑ | |
| 14 | THF | ↑ |

TABLE 2-continued

| | | |
|---|---|---|
| 15 | DMF | [acetate ester of 7-(naphthalen-2-yl)heptan-1-ol] |
| 16 | DMA | ↑ |
| 17 | ↑ | ↑ |
| 18 | NMP | ↑ |
| 19 | ↑ | ↑ |
| 20 | Diglyme | [1-(3,5-difluorophenyl)undecan-5-one structure] |
| 21 | DMA | ↑ |
| 22 | ↑ | [1-butyl-3-(4-cyclohexylbutyl)benzene] |
| 23 | ↑ | [(4-cyclohexylbutyl)benzene] |
| 24 | ↑ | [4-(4-cyclohexylbutyl)benzonitrile] |
| 25 | ↑ | [fluorinated chain with 4-methoxyphenyl] |
| 26 | NMP | [fluorinated chain with 3-acetoxyphenyl] |
| 27 | ↑ | [branched nitrile benzyl compound] |
| 28 | DMF | [2-propyl-octylbenzene] |

TABLE 2-continued

| 29 | ↑ | ↑ |
| 30 | DMA |  |
| 31 | NMP | |
| 32 | DMA | ↑ |
| 33 | DMF | |
| 34 | DMA | |

Comparative Example 1

In Comparative example 1, the experiment was conducted in a similar manner as in Example 1 except that 0.015 mmol (6.0 mg) of tri(t-butyl)phosphine was used instead of 1,10-phenanthroline. Yield of 4-octylanisole was 5%.

What is claimed is:
1. A method for producing a coupling compound of formula (1):

$$(Y-)_{(n-1)}R^1-R^2-(R^1)_{(n'-1)} \quad (1)$$

wherein $R^1$, $R^2$ n and n' are as defined below,
Y is $R^2$ X as defined below,
which method comprises reacting
an organic halogen compound of formula (2):

$$n'(R^1X^1{}_n) \quad (2)$$

wherein $X^1$ represents a bromine or iodine,
$R^1$ represents a substituted or unsubstituted, linear, branched or cyclic hydrocarbon group of which α and β carbon atoms in relation to $X^1$ are sp3 carbon atoms,
n and n' each independently represent an integer of 1 or 2, and provided that n and n' do not simultaneously represent 2,
with an organic boron compound of formula (3):

$$m\{R^2(BX^2{}_2)_{n'}\} \quad (3)$$

wherein $R^2$ represents a substituted or unsubstituted aryl group, a substituted or unsubstituted heteroaryl group, or a substituted or unsubstituted alkenyl group and the boron atom is bonded with a sp2 carbon atom thereof,
$X^2$ represents a hydroxyl or alkoxy group,
n' is as defined above,
m represents an integer of 1 or 2, and m is not more than n,
in the presence of a catalyst comprising
a) a nickel compound, and
b) b-1) a compound of formula (i):

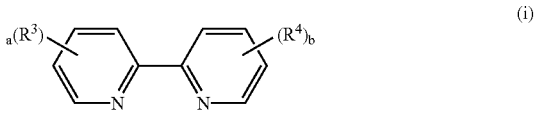

wherein $R^3$ and $R^4$ each independently represent
an alkyl, aryl, alkenyl, alkynyl, alkoxyl, hydroxy, hydroxyalkyl, sulfo, alkyloxycarbonyl, aryloxycarbonyl, carbamoyl, cyano, isocyano, cyanato, isocyanato or formyl group, or a hydrocarbylsilyl group, and
optionally two adjacent groups among $R^3$ and $R^4$ groups with the carbon atoms to which they are bonded form a ring, a and b are the same or different and independently represent an integer of 0 to 4, or b-2) a compound of formula (ii):

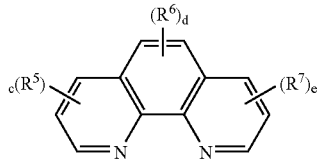

wherein $R^5$, $R^6$ and $R^7$ groups are the same or different and independently represent an alkyl, aryl, alkenyl, alkynyl, alkoxyl, hydroxy, sulfo, alkyloxycarbonyl, aryloxycarbonyl, carbamoyl, cyano, isocyano, cyanato, isocyanato or formyl group, or a hydrocarbylsilyl group, and optionally two adjacent groups among $R^5$, $R^6$, and $R^7$ groups with the carbon atoms to which they are bonded form a ring, c, and e are the same or different and independently represent an integer of 0 to 3, and d represents an integer of 0 to 2; or a mixture thereof.

2. A method according to claim 1, wherein the organic boron compound of formula (3) is a boron compound of formula (4):

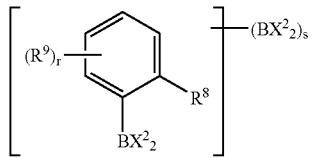

wherein $R^8$ represents a hydrogen atom, r represents an integer of 0 to 4, s represents an integer of 0 or 1, $R^9$ is the same or different and independently represents a substituted or unsubstituted aryl group, a subtituted or unsubstituted heteoaryl group, or a substituted or unsubstituted linear, branched, or cyclic alkenyl group, or $R^9$ groups bonded with adjacent carbon atoms of the benzene ring together with the benzene ring form an orth, or ortho, peri condensed polycyclic aromatic ring, $X^2$ represents a hydroxyl or alkoxy group, or $X^2{}_2$ groups together form an alkylendioxy group, or a boronic acid trimer thereof, and $r+s \leq 4$ when the benzene ring does not form a condensed polycyclic aromatic ring.

3. A method according to claim 1, wherein the nickel compound is a nickel salt, or $\pi$ complex compound of zero or divalent nickel.

4. A method according to claim 1, wherein $R^3$ and $R^4$ are alkyl and a and b are 1 or 2.

5. A method according to claim 1, wherein a and b are 0.

6. A method according to claim 1, wherein $R^5$ to $R^7$ are alkyl, and c, d and e are 1 or 2.

7. A method according to claim 3, wherein c, d and e are 0.

8. A method according to claim 1, wherein the compound of formula (i) is dipyridyl, 4,4'-dimethyl-2,2'-dipyridyl, 4,4'-diphenyl-,2,2'-dipyridyl, 5,5-dimethyl-2,2'-dipyridyl, 4,4'-di-t-butyl-2,2'-dipyridyl, 6-methyl-2,2-dipyridyl, 2,2'-biquinoline, 6,6'-bi-2-picoline, 2,2'-bi-4-lepidine, 4,4'-dinonyl-2,2'-dipyridyl, 2,2'-dipyridyl-3,3'-diol, 2,2'-biquinolinyl-4,4'-dicarboxylic acid dibutyl ester, or 4,4' dimethoxy-2,2'-dipyridyl, and the compound of formula (ii) is 2,9-dimethyl-4,7diphenyl-1,10-phenanthroline, 2,9-dimethyl-1,10-phenanthroline, 3,4,7,8-tetramethyl-1,10-phenanthroline, 4,7-dihydroxy-1,10-phenanthroline, 4,7-diphenyl-1,10-phenanthroline, 4-methyl-1,10-phenanthroline, 5-methy-1,10-phenanthroline, 5-phenyl-1,10-phenanthroline, 4,7-dimethyl-1,10-phenanthroline, 5,6-dimethyl-1,10-phenanthroline, 1,10-phenanthroline-2,9-dimethanol, or 2,9-di-n-butyl-1,10-phenanthroline.

* * * * *